US008153829B2

(12) United States Patent
Lemaire et al.

(10) Patent No.: US 8,153,829 B2
(45) Date of Patent: Apr. 10, 2012

(54) METHODS FOR THE PREPARATION OF HEXAHYDROFURO[2,3-B]FURAN-3-OL

(75) Inventors: Sébastien François Emmanuel Lemaire, Brussels (BE); Andras Horvath, Turnhout (BE); Wim Albert Alex Aelterman, Gierle (BE); Thomas Joachim Landewald Rammeloo, Vosselaar (BE)

(73) Assignee: Janssen Pharmaceutica N.V., Beerse (BE)

( * ) Notice: Subject to any disclaimer, the term of this patent is extended or adjusted under 35 U.S.C. 154(b) by 422 days.

(21) Appl. No.: 12/447,537

(22) PCT Filed: Nov. 9, 2007

(86) PCT No.: PCT/EP2007/062119
§ 371 (c)(1),
(2), (4) Date: Apr. 28, 2009

(87) PCT Pub. No.: WO2008/055970
PCT Pub. Date: May 15, 2008

(65) Prior Publication Data
US 2010/0094028 A1    Apr. 15, 2010

(30) Foreign Application Priority Data
Nov. 9, 2006 (EP) .................... 06123752

(51) Int. Cl.
*C07D 307/20* (2006.01)
*C07D 493/04* (2006.01)
(52) U.S. Cl. ........................ 549/475; 549/464
(58) Field of Classification Search .......... 549/464, 549/475
See application file for complete search history.

(56) References Cited

U.S. PATENT DOCUMENTS

| 6,127,372 A | 10/2000 | Tung et al. |
| 6,867,321 B2 | 3/2005 | Ikemoto et al. |
| 7,700,645 B2 * | 4/2010 | Vermeersch et al. ......... 514/456 |
| 2004/0162340 A1 | 8/2004 | Ikemoto et al. |

FOREIGN PATENT DOCUMENTS

| EP | 0 715 618 A1 | 6/1996 |
| EP | 0 754 669 A1 | 1/1997 |
| EP | 1 029 856 A1 | 8/2000 |
| EP | 1 067 125 A1 | 1/2001 |
| EP | 1 081 133 A1 | 3/2001 |
| EP | 1 215 209 A1 | 6/2002 |
| WO | WO 95/06030 A1 | 3/1995 |
| WO | WO-95/24385 A1 | 9/1995 |
| WO | WO-97/18205 A1 | 5/1997 |
| WO | WO-99/65870 A2 | 12/1999 |
| WO | WO-99/67254 A2 | 12/1999 |
| WO | WO-99/67417 A2 | 12/1999 |
| WO | WO-00/47551 A2 | 8/2000 |
| WO | WO-00/76961 A1 | 12/2000 |
| WO | WO-01/25240 A1 | 4/2001 |
| WO | WO-02/060905 A2 | 8/2002 |
| WO | WO 03/022853 | 3/2003 |
| WO | WO-03/024974 A2 | 3/2003 |
| WO | WO 2004/002975 | 1/2004 |
| WO | WO-2004/033462 A2 | 4/2004 |
| WO | WO-2005/063770 A1 | 7/2005 |
| WO | WO-2005/095410 A1 | 10/2005 |

OTHER PUBLICATIONS

Ghosh, A.K. et al. "T1C14 Promoted Three Component Coupling Reaction: A New Method for the Synthesis of Functionalized Tetrahydrofurans and Tetrahydropyrans". Tetrahedron Letters, Elsevier, Amsterdam, NL., vol. 40, No. 6. Feb. 5, 1999, pp. 1083-1086, XP00415464.
Ghosh, A.K. et al. "Potent HIV Protease Inhibitors Incorporating High-Affinity P2-Ligands and (R)-(Hydroxyethylamino)Sulfonamide Isostere". BioOrganic & Medicinal Chemistry Letters, Oxford, GB, vol. 8, No. 6, Mar. 17, 1998, pp. 687-690,XP004136945.
Boyer et al., A New Method for the Reduction of Esters, *Synthesis*, 558-559, 1981.
Chuit et al., Improved Procedure for the Selective Reduction of Carbonyl Compounds and Carboxylic Acid Esters by Potassium Salt-Induced Hydrosilylation, *Synthesis*, 981-984, 1982.
Drew et al., A Convenient Procedure for the Reduction of Esters, Carboxylic Acids, Ketones and Aldehydes using Tetrabutylammonium Fluoride (or Triton® B) and Polymethylhydrosiloxane, *Synlett*, 989-997, 1997.
Ghosh et al., Nonpeptidal $P_2$ Ligands for HIV Protease Inhibitors: Structure-Based Design, Synthesis, and Biological Evaluation, *J. Med. Chem.*, 39(17):3278-3290, 1996.
Ghosh et al, Stereoselective Photochemical 1,3-Dioxolane Addition to 5-Alkoxymethyl-2(5H)-furanone: Synthesis of Bistetrahydrofuranyl Ligand for HIV Protease Inhibitor UIC-94017 (TMC-114), *J. Org. Chem.*, 69(23):7822-7829, 2004.
Ghosh et al., Synthesis and Optical Resolution of High Affinity $P_2$-Ligands for HIV-1 Protease Inhibitors, *Tetrahedron Letters*, 36(4):505-508, 1995.
Igarashi et al., Ruthenium Complex Catalyzed Hydrosilylation of Esters: a Facile Transformation of Esters to Alkyl Silyl Acetals and Aldehydes, *Tetrahedron Letters*, 42:2149-2151, 2001.
Marc, Reactions, Mechanisms, and Structure; *Advanced Organic Chemistry* 3rd Ed., 368-369, 1985.
McManus et al., The Synthesis of Aminoalcohols from Epoxides and Ammonia, *Synthetic Communications*, 3(3):177-180, 1973.
Mikami et al., Catalytic Asymmetric Glyoxylate-Ene Reaction: A Practical Access to α-Hydroxy Esters in High Enantiomeric Purities, *J.Am. Chem. Soc.*, 112(10):3949-3954, 1990.
Mimoun, Selective Reduction of Carbonyl Compounds by Polymethylhydrosiloxane in the Presence of Metal Hydride Catalysts, *J. Org. Chem.*, 64(7):2582-2589, 1999.

(Continued)

*Primary Examiner* — Bernard Dentz
(74) *Attorney, Agent, or Firm* — Woodcock Washburn LLP

(57) ABSTRACT

Methods for the preparation of hexahydrofuro[2,3-b]furan-3-ol and especially its enantiomer (3R,3aS,6aR) hexahydrofuro[2,3-b]furan-3-ol, as well as certain novel intermediates for use in such methods are disclosed.

20 Claims, No Drawings

OTHER PUBLICATIONS

Reding et al., An Inexpensive Air-Stable Titanium-Based System for the Conversion of Esters to Primary Alcohols, *J. Org. Chem.*, 60(24):7884-7890, 1995.

Reetz et al., Chemoselective Addition of Organotitanium Reagents to Carbonyl Compounds, *Chemische Berichte*, 118:1421-1440, 1985.

Theodora W. Greene, *Protective Groups in Organic Synthesis*, Table of Contents, John Wiley and Sons, Inc., 1981 (New York).

Zhang, et al., Efficient Homogeneous Catalytic Hydrogentation of Esters to Alcohols, *Angewandte Chemie*, 45:1113-1115, 2006.

* cited by examiner

METHODS FOR THE PREPARATION OF HEXAHYDROFURO[2,3-B]FURAN-3-OL

The present invention relates to methods for the preparation of hexahydrofuro[2,3-b]-furan-3-ol and especially its enantiomer (3R,3aS,6aR) hexahydrofuro[2,3-b]furan-3-ol, as well as certain novel intermediates for use in such methods.

The (3R,3aS,6aR) hexahydrofuro[2,3-b]furan-3-oxy radical is an important pharmacological moiety present in the structure of retroviral protease inhibitors such as those described by Ghosh et al in J. Med. Chem. 1996, 39(17), 3278-3290, and also those described in WO 95/24385, WO 99/65870, WO 99/67254, WO 99/67417, WO-00/47551, WO 00/76961, WO 01/25240, U.S. Pat. No. 6,127,372 and EP 0 715 618. Said publications are herein incorporated by reference. One such protease inhibitor which has been approved in the USA for human clinical use for the treatment of retroviral infections and having the above structural moiety is the compound having the USAN approved name darunavir with the chemical name [(1S,2R)-3-[[(4-aminophenyl)-sulfonyl](2-methylpropyl)amino]-2-hydroxy-1-(phenylmethyl)propyl]-carbamic acid (3R,3aS,6aR) hexahydrofuro[2,3-b]furan-3-yl ester and the structure of formula (A):

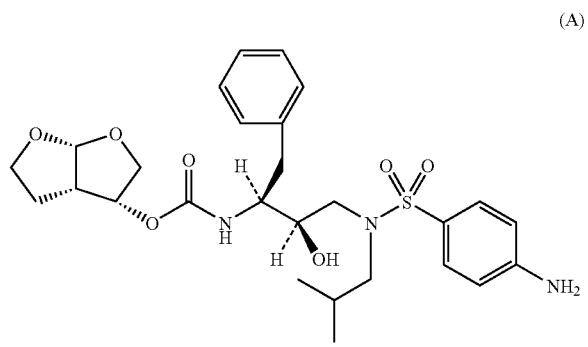

An important precursor in the synthesis of the protease inhibitors described above and containing the hexahydrofuro[2,3-b]furan-3-oxy radical is the compound hexahydrofuro[2,3-b]furan-3-ol of formula (I):

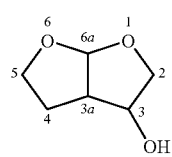

Despite the fact that hexahydrofuro[2,3-b]furan-3-ol has three stereogenic centres and theoretically eight different stereoisomers should occur, only four stereoisomers are deemed to exist. This is due to the rigidity of the bicyclic ring structure in hexahydrofuro[2,3-b]furan-3-ol which causes the trans-fused stereoisomers thereof to be thermodynamically unfavourable. Only stereoisomers having a cis-fused configuration are thermodynamically stable, reducing the number of stereoisomers of hexahydrofuro-[2,3-b]furan-3-ol to the endo and exo diastereoisomers, each comprising a pair of enantiomers as shown below:

endo:

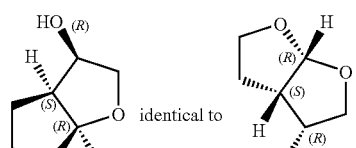

3R, 3aS, 6aR

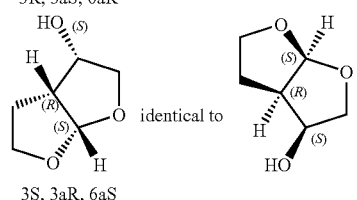

3S, 3aR, 6aS exo:

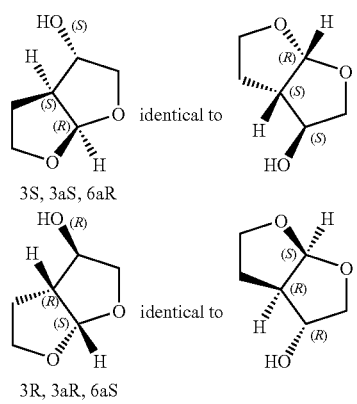

3S, 3aS, 6aR 3R, 3aR, 6aS

More particularly for the preparation of those protease inhibitors containing the enantiomeric (3R,3aS,6aR) hexahydrofuro[2,3-b]furan-3-oxy radical such as the protease inhibitor darunavir referred to above the (3R,3aS,6aR) enantiomer of formula (Ia), is particularly useful:

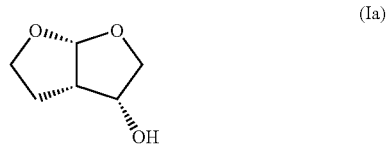

In view of the potential importance of the above protease inhibitors and the consequent need to manufacture these compounds on a commercial scale there have been numerous proposals in the literature for methods by which the compounds of formulae (I) and (Ia) above can be prepared.

Many such proposals have involved the formation of the bicyclic bis-furan structure starting from non-cyclic precursors for example involving the intermediate formation of a lactone intermediate and then reduction and cyclisation such as those processes described in WO 03/022853, US 2004/0162340, WO 2004/033462, U.S. Pat. No. 6,867,321, WO-2005/095410 and also Ghosh et al, J. Org Chem. 2004, 69, 7822-7829. These processes involve a relatively large number of steps and in some cases the formation of a nitromethyl intermediate, requiring the use of nitromethane which is a hazardous reagent. Another approach described in WO 02/060905 involves the reaction of 2,3-dihydrofuran with an alkynyl derivative to form a 2-alkynyloxy furan derivative which is then cyclised in the presence of irradiated light. The use of light is however unsuitable for practice of the process on an industrial scale. The use of light is also required in the process described in WO 03/024974 where furan is reacted with a carbonyl derivative in the presence of light. WO 2004/002975 describes a process starting from 2,3-dihydrofuran which is reacted for example with a chloroglyoxylate ester to effect introduction of the glyoxylate grouping at the 3-position of the furan ring and then reduction to form a 1,2-dihydroxyethyl side-chain followed by treatment for example with a halogenating agent to form a 3a-halo-hexahydrofuro-[2,3-b]furan-3-ol compound which is subsequently reduced. This process also suffers from the disadvantage that it requires numerous steps from the furan starting material which is uneconomic on an industrial scale.

A similar approach is proposed by Ghosh et al in Tetrahedron Letters 40 (1999) 1083-1086 involving the reaction of 2,3-dihydrofuran with ethyl glyoxylate with titanium tetrachloride to provide an oxonium ion intermediate which is then reacted with a nucleophile to provide 3-(β-carboethoxy-α-hydroxymethyl)-2-substituted tetrahydrofuran derivatives. Examples of such nucleophiles comprise silyl derivatives and methanol. In the only example described a mixture of ethyl glyoxylate and 2,3-dihydrofuran in dichloromethane was added to a solution of titanium tetrachloride in dichloromethane at −78° C. and stirred for one hour. Allyltrimethylsilane was added to the mixture at −78° C. and the resulting mixture stirred at −78° C. to 23° C. for one hour. The reaction was quenched with aqueous sodium hydrogen carbonate solution and extracted with ethyl acetate, and the combined organic layers dried, concentrated and then purified by flash chromatography. This process suffers from certain disadvantages for example the use of a very low reaction temperature of −78° C. which is not practically possible on an industrial scale. Moreover we have found that the use of the titanium tetrachloride process described Ghosh et al presents problems with subsequent working up to ensure the efficient removal of the titanium compound, the removal of titanium salt being essential to avoid impurities and side-reactions in subsequent stages.

It is an object of the invention to provide a new and improved synthesis for the production of hexahydrofuro[2,3-b]furan-3-ol. It is a further object of the invention to provide such a synthesis which employs readily available and economic starting materials and uses reaction conditions which are readily achievable on an industrial scale. It is a further object of the present invention to provide a convenient method for the production of 3-(β-carboethoxy-α-hydroxymethyl)-2-substituted tetrahydrofuran derivatives and analogs thereof. It is a further object of the invention to provide new and useful intermediates useful in the synthesis of hexahydrofuro[2,3-b]furan-3-ol. It is a further object of the invention to provide a new and improved synthesis of (3R, 3aS,6aR) hexahydrofuro[2,3-b]furan-3-ol useful in the production of antiretroviral protease inhibitors.

It has been found that the use of certain titanium salts other than the titanium tetrachloride salt used by Ghosh et al in the process described above provides certain advantages as discussed below. We have also found that the purification of the crude 3-(β-carboethoxy-α-hydroxymethyl)-2-substituted tetrahydrofuran product can be improved by the use of certain agents, i.e. water-soluble complexing agents (e.g. Rochelle salt or diethanolamine) to quench the reaction and to remove titanium species which may be deleterious in subsequent stages. Thus the use of water soluble complexing agents instead of sodium hydrogen carbonate described by Ghosh et al results in significant improvements in the quality of the resulting product.

The use of the above process and the subsequent conversion of the resulting 3-(β-carboethoxy-α-hydroxymethyl)-2-substituted tetrahydrofuran product provides a useful synthetic route to hexahydrofuro[2,3-b]furan-3-ol and its (3R, 3aS,6aR) enantiomer in a relatively small number of stages in comparison with prior art processes and using economic starting materials and reactions conditions which provide the final product and intermediates in good yield and purity.

According to one feature of the present invention we provide a process for the preparation of a compound of formula (V) which comprises reacting 2,3-dihydrofuran of formula (II) with a glyoxylate derivative of formula (III) in the presence of a titanium salt of formula $Ti(Hal)_n(OR)_{4-n}$ in which Hal is a halogen radical, n is 0, 1, 2 or 3 and R is alkyl or arylalkyl, and subsequently reacting the resulting reaction product with an alcohol of formula (IV) to form a compound of formula (V):

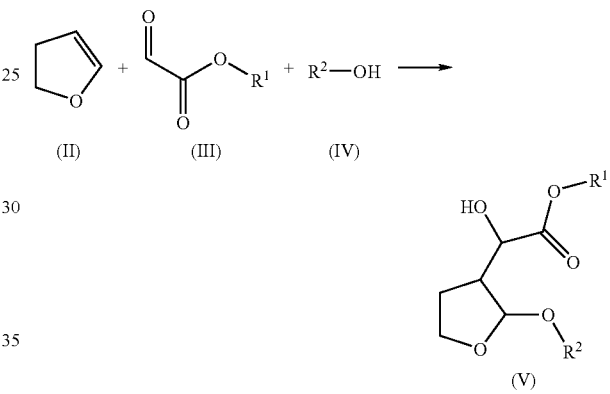

in which $R^1$ is alkyl or arylalkyl and $R^2$ is alkyl or arylalkyl.

The glyoxylate derivative of formula (III) is preferably a compound in which $R^1$ is a $C_{1-4}$ alkyl group especially an ethyl group, or a phenyl$C_{1-4}$alkyl group especially a benzyl group. The titanium salt is preferably a salt of formula $Ti(Hal)_n(OR)_{4-n}$ in which Hal is a chlorine or bromine atom especially a chlorine atom and R is a $C_{1-4}$alkyl group for example a propyl group preferably an iso-propyl group, or an arylalkyl group for example a phenyl$C_{1-4}$alkyl group and especially benzyl and n is 1 or 2 especially 2; a particularly preferred titanium salt for use in accordance with the present invention is $TiCl_2(OiPr)_2$. It will appreciated that such titanium salts can be formed in situ in the reaction mixture for example by reacting an appropriate titanium halide with an appropriate $Ti(OR)_4$ compound. The particular titanium salt formed will depend on the amount of the $Ti(OR)_4$ compound added to the titanium halide, for example the addition of one third of an equivalent of the $Ti(OR)_4$ compound will result in formation of the $TiHal_3(OR)$ compound. The above preferred $TiCl_2(OiPr)_2$ salt can be prepared in situ by the addition of $TiCl_4$ and $Ti(OiPr)_4$ to the reaction mixture. A method for the preparation of the above $TiCl_2(OiPr)_2$ compound is described by Mikami et al, J. Am. Chem. Soc., 1990, 112, 3949-3954. A method for the preparation of $TiCl(OiPr)_3$ is described by Reetz et al, Chemische Berichte, 1985, 118, 1421-1440. Other titanium compounds of formula $Ti(Hal)_n(OR)_{4-n}$ can be prepared in analogous manner.

It has been found that the presence of at least one Hal group in the titanium compound is generally required as the process has been found to be less effective if a compound of formula Ti(OR)$_4$ is used. In the titanium compound n is therefore preferably 1, 2 or 3. A compound of formula Ti(OR)$_4$ is generally used in conjunction with titanium tetrachloride to generate a compound of formula Ti(Hal)$_n$(OR)$_{4-n}$ in which n is 1, 2 or 3.

The use of the above titanium compounds has been found to be particularly advantageous over the titanium tetrachloride salt used by Ghosh et al as the latter salt is an unstable corrosive liquid whereas the titanium compounds used in the process according to the invention are generally stable solids and are therefore significantly more convenient to handle in an industrial process. Moreover the use of titanium tetrachloride as described by Ghosh et al has been found to lead to unacceptably high residual amounts of titanium by-products in the reaction mixture which may result in later stages of the synthesis of hexahydrofuro[2,3-b]furan-3-ol being inoperable or having very low yields.

The alcohol of formula (IV) is preferably a C$_{1-4}$alkanol such as methanol, ethanol or a propanol especially iso-propanol, or a phenylC$_{1-4}$alkanol such benzyl alcohol.

Both the initial reaction of 2,3-dihydrofuran with the glyoxylate derivative and the subsequent reaction with the alcohol of formula (IV) are generally carried out in an organic solvent preferably an aprotic solvent such as dichloromethane, ethyl acetate, 1,2-dichlorethane, tetrahydrofuran (THF) or 2-methyl-tetrahydrofuran.

These reactions are conveniently carried out at a temperature of at least −20° C., preferably at least −10° C. and especially at least −5° C., room temperature being generally preferred. The use of such temperatures contrasts with the use of a temperature of −78° C. described by Ghosh et al in the Tetrahedron Letters procedure referred to above. The former more elevated temperatures employed in accordance with the present invention are significantly more convenient for operation of the process on an industrial scale.

A further advantage of the process according to the invention over the process described by Ghosh et al is that we have found that the titanium compound can be used in less than stoichiometric amounts for example 0.5 equivalent or less whereas the Ghosh process requires the use of an equivalent amount of the titanium compound. The use of lower amounts of titanium is more economical and leads to lower amounts of by-products that require disposal and our process is therefore advantageous from an environmental viewpoint.

Upon completion of the reaction with the alcohol of formula (IV) the reaction mixture is generally treated with an alkaline reagent to quench or terminate any further reactions and the formation of by-products, the alkaline reagent generally providing a pH of 8-11 preferably about 10. In the Ghosh et al Tetrahedron Letters process an aqueous solution of sodium hydrogen carbonate is used to quench the reaction. However we have found that the use of a water-soluble complexing agent as an alternative quenching reagent provides a significantly improved work-up. Both ionic compounds such as Rochelle salt (sodium potassium tartrate, tetrahydrate) or neutral organic molecules such as diethanolamine may be used as the water-soluble complexing agent. Thus the addition of Rochelle salt or diethanolamine in an aqueous solution to the organic reaction mixture obtained in the above process quenches the reaction and enables any residual titanium compound to be readily separated in the aqueous phase, leaving the organic phase containing the desired compound of formula (V) which routinely contains less than 5 ppm of titanium compound. The resulting compound of formula (V) is obtained as a mixture of stereoisomeric forms and can be used as such for the next stage in the synthesis of hexahydrofuro [2,3-b]furan-3-ol.

The above process starting from 2,3-dihydrofuran provides the desired compound of formula (V) in high or even quantitative yields and with good quality using reagents which are readily available from commercial sources and reaction conditions which can be used on an industrial scale.

The term "alkyl" alone or in combination with any other term refers, except where otherwise specified, to straight-chain or branched-chain saturated aliphatic hydrocarbon radicals or, in the event that at least three carbon atoms are present, cyclic saturated aliphatic hydrocarbon radicals, containing 1 to 10 carbon atoms, preferably 1 to 8 carbon atoms, more preferably 1 to 6 carbon atoms or even more preferably 1 to 4 carbon atoms. Examples of such radicals include but are not limited to, methyl, ethyl, n-propyl, iso-propyl, n-butyl, iso-butyl, sec-butyl, tert-butyl, pentyl, iso-pentyl, n-hexyl, cyclopropyl, cyclobutyl, cyclopentyl, cyclohexyl and the like.

The term "aryl" alone or in combination with any other term, refers to a carbocyclic aromatic moiety and includes monocyclic, bicyclic and other polycyclic radicals. Examples of aryl radicals include but are not limited to phenyl and naphthyl radicals.

The term "halogen" refers to a fluorine, chlorine, bromine or iodine atom.

The term "stereoisomeric forms" as used herein defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. Except where specified, all stereoisomeric forms of the compounds employed in the present invention both in pure form or in admixture with each other are intended to be embraced within the scope of the present invention.

Pure stereoisomeric forms of the compounds mentioned herein, i.e. where a particular stereoisomeric form is specified, are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds having a stereoisomeric excess of 90% up to 100%, even more in particular having a stereoisomeric excess of 94% up to 100% and most in particular having a stereoisomeric excess of 97% up to 100%.

Pure stereoisomeric forms of the compounds mentioned herein may be obtained by the application of art-known procedures. For instance, enantiomers may be separated from each other by the selective crystallization of their diastereomeric salts with optically active acids. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereoselectively. Preferably, if a specific stereoisomer is desired, said compound will be synthesized by stereoselective methods of preparation. These methods will advantageously employ enantiomerically pure starting materials.

The resulting compound of formula (V) obtained in the above process can be used in the next stage of the synthesis of hexahydrofuro[2,3-b]furan-3-ol without the need to separate or isolate its stereoisomers.

The above compounds of formula (V) with the exception of those compounds in which $R^1$ is methyl or ethyl and $R^2$ is methyl are novel compounds and therefore we provide as a further feature of the invention compounds of formula (Va):

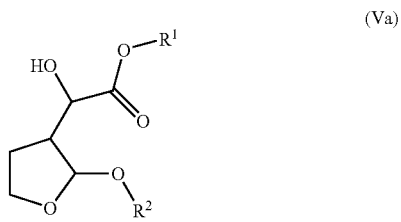

(Va)

and the stereoisomeric forms and racemic mixtures thereof, in which $R^1$ is alkyl or arylalkyl and $R^2$ is alkyl or arylalkyl, providing that when $R^2$ is methyl $R^1$ is not methyl or ethyl. $R^1$ is preferably a $C_{1-4}$ alkyl group such as propyl especially iso-propyl, or a phenyl$C_{1-4}$ alkyl group especially a benzyl group. $R^2$ is preferably a $C_{1-4}$alkyl group such as ethyl or propyl especially iso-propyl, or a phenyl$C_{1-4}$alkyl group such as benzyl. Compounds of formula (V) in which $R^1$ is ethyl or methyl and $R^2$ is methyl are disclosed in Ghosh et al in Tetrahedron Letters 40 (1999) 1083-1086 referred to above.

The compounds of formula (V) are thus useful as intermediates in the preparation of compounds of formula (I). An especially useful compound of formula (V) is ethyl hydroxy-(2-isopropoxytetrahydro-3-furanyl)acetate.

According to further feature of the present invention we provide a process for the preparation of compounds of formula (VI) which comprises reducing a compound of formula (V) to form a compound of formula (VI):

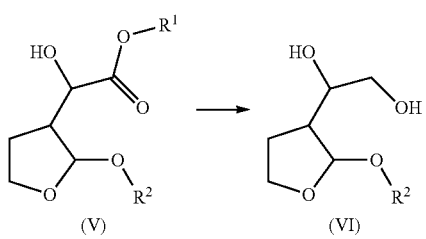

The reduction of the compound of formula (V) is generally performed using a hydride reducing agent such as an alkali metal borohydride such as lithium borohydride, sodium borohydride, potassium borohydride, sodium acetoxyborohydride, sodium triacetoxyborohydride or sodium cyanoborohydride, an aluminium hydride reducing agent such as lithium aluminium hydride, DibalH (di-isobutyl aluminium hydride) or aluminium hydride, or zinc borohydride. Alternatively the reduction can be effected by catalytic hydrogenation. The hydrogenation may be conducted using a heterogeneous catalyst such as an activated nickel catalyst for example the catalyst commercially available from Degussa as B 111W, an activated nickel catalyst doped with molybdenum or chromium/iron for example the catalyst commercially available from Degussa as BK 113W, or an activated copper catalyst for example the catalyst commercially available from Degussa as B3113. The hydrogenation can also be effected using a homogeneous catalyst such as ruthenium in accordance with the procedure of Milstein, ACIE 2006, 45, 1113. The reduction can also be performed by hydrosilylation for example using polymethylhydrosiloxane (PMHS) or triethylsilane for example in combination with a Zn (II) catalyst (Mimoun, J. Org. Chem., 1999, 64, 2582-2589, a ruthenium catalyst (Fuchikami et al, Tetrahedron Letters, 42 (2001), 2149-2151), tetrabutylammonium fluoride (TBAF or Triton B) (Lawrence et al, Synlet, 1997, 989-991), potassium fluoride or cesium fluoride (Coriu et al, Synthesis, 1982, 981 and 1981, 558) or a titanium (IV) catalyst (Redding and Buchwald, J. Org. Chem. 1995, 60, 7884-7890).

Sodium borohydride is especially preferred as the reducing agent. The reduction is generally conducted in an organic solvent conveniently a polar solvent such as ethanol or tetrahydrofuran. When a borohydride reducing agent is used, after completion of the reduction it is desirable to quench the reaction with a complexing compound to complex any residual boron compound in the reaction mixture and to avoid further side-reactions and the formation of unwanted by-products. We have found that treatment of the reaction mixture with diethanolamine, for example in the form of its hydrochloride, as a quenching reagent provides especially good results in terms of the purity of the desired final product. Alternatively ammonium chloride can advantageously be used to quench the reaction. The resulting compound of formula (VI) is obtained as a mixture of stereoisomeric forms and can be used as such for the next stage in the synthesis of hexahydrofuro[2,3-b]furan-3-ol.

The above compounds of formula (VI) are novel compounds and therefore we provide as a further feature of the invention compounds of formula (VI):

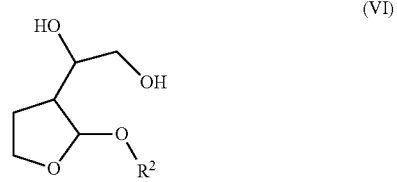

(VI)

and stereoisomeric forms and racemic mixtures thereof, in which $R^2$ is alkyl or arylalkyl preferably a $C_{1-4}$alkyl group such as methyl, ethyl or propyl especially iso-propyl, or a phenyl$C_{1-4}$alkyl group such as benzyl.

An especially preferred novel compound of formula (VI) is 1-(2-iso-propoxytetrahydro-3-furanyl)-1,2-ethanediol.

The compounds of formula (VI) are thus useful as intermediates in the synthesis of compounds of formulae (I) and (Ia).

According to further feature of the present invention we provide a process for the preparation of a compound of formula (I) which comprises cyclising a compound of formula (VI) to form a compound of formula (I):

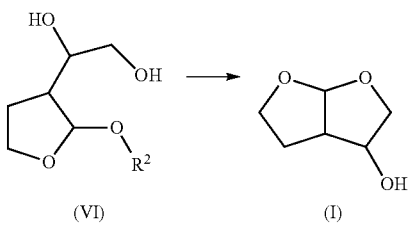

in which $R^2$ is preferably a $C_{1-4}$alkyl group such as methyl, ethyl or propyl especially iso-propyl, or a phenyl$C_{1-4}$alkyl group such as benzyl.

The cyclisation of the compound of formula (VI) can be effected for example by treatment with an acid generally a strong protic acid such as hydrochloric acid, p-toluene-sulfonic acid, methanesulfonic acid, camphosulfonic acid, amberlyst resin, TFA, p-bromobenzensulfonic acid or acetic acid. The reaction is generally carried out in an organic solvent for example a polar solvent such as tetrahydrofuran, dichloromethane, ethyl acetate, ethanol, methanol or acetone conveniently at a temperature of −20° C. to 50° C. When tetrahydrofuran is used, the preferred temperature is between 40° C. and 50° C., preferably 45° C. A base such as triethylamine or pyridine is subsequently added to neutralise the reaction mixture and terminate the reaction. The process results in a mixture of two diastereoisomers of formula (I), namely the endo diastereoisomer comprising the 3R,3aS,6aR and 3S,3aR,6aS enantiomers and the exo diastereoisomer comprising the 3S,3aS,6aR and 3R,3aR,6aS enantiomers referred to above. The two diastereoisomers can be readily separated in conventional manner for example by chromatography on silica gel using a petroleum ether/ethyl acetate (1/9) mixture as an eluant.

After separation of the above diastereoisomers the endo diastereoisomer can be directly used in the preparation of protease inhibitors where this stereoisomeric moiety is required if desired after separation into its constituent enantiomers in conventional manner for example in accordance with the method described by Ghosh et al in Tetrahedron Letters, Vol 36, No. 4, 505-508, 1995, or WO 02/060905, by acylation with for example an acid chloride or anhydride, conveniently in an aprotic solvent such as tetrahydrofuran or dichloromethane and in the presence of a base such as sodium carbonate or triethylamine. The resulting mixture of esters is then reacted with an appropriate esterase enzyme such lipase Ps30 under conditions which permit the reaction of predominantly one of the racemic esters to provide a mixture of an alcohol of predominantly one enantiomer and the remaining unreacted ester consistently predominantly of the other enantiomer. The mixture of alcohol and ester may then be separated in conventional manner for example by silica gel chromatography. The enantiomeric unreacted ester can be converted to the corresponding alcohol for example by reaction with methyllithium in tetrahydrofuran.

If desired the exo diastereoisomer can be converted into the endo diastereoisomer in conventional manner for example as described by Ghosh et al in J. Org. Chem. 2004, 69, 7822-7829, by an oxidation/reduction sequence involving intermediate formation of a ketone of formula (I'):

Thus in accordance with the method of Ghosh et al above the exo diastereoisomer is oxidised to the ketone of formula (I') with tetrapropylammonium perrhuthenate (TPAP) and 4-methylmorpholino-N-oxide (NMO) and the resulting ketone is reduced for example with a hydride reducing agent such as sodium borohydride in an organic solvent for example a polar solvent such as ethanol to provide the corresponding endo diastereoisomer. Alternatively the above oxidation can be effected with NaOCl/2,2,6,6-tetramethylpiperidine 1-oxide (TEMPO).

It will be appreciated that the above oxidation and reduction procedure can also be effected starting from a mixture of the endo and exo forms, thereby avoiding the need to carry out any prior separation of the diastereoisomers.

According to a further feature of the invention we provide a process for the preparation of hexahydrofuro[2,3-b]furan-3-ol which comprises the stages of:

a) reacting 2,3-dihydrofuran of formula (II) with a glyoxylate derivative of formula (III) in the presence of a titanium salt of formula Ti(Hal)$_n$(OR)$_{4-n}$ in which n is 0, 1, 2 or 3 and R is alkyl or arylalkyl, and subsequently reacting the resulting reaction product with an alcohol of formula (IV) to form a compound of formula (V):

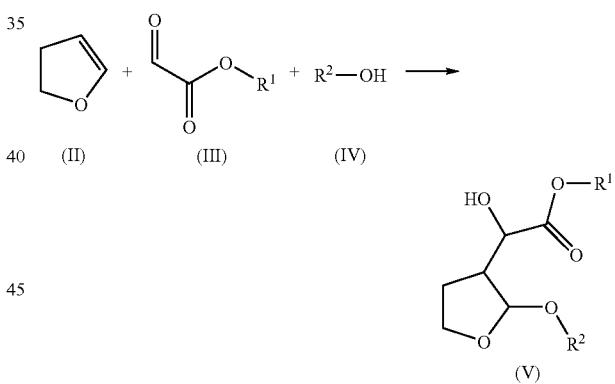

in which $R^1$ is alkyl or arylalkyl and $R^2$ is alkyl or arylalkyl; and b) reducing the resulting compound of formula (V) to form a compound of formula (VI):

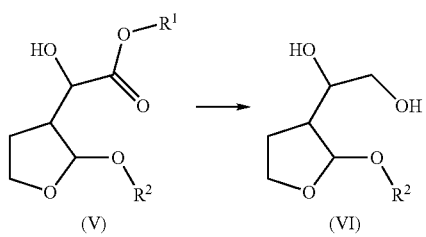

and
c) cyclising a compound of formula (VI) to form a compound of formula (I):

(VI) → (I)

and if desired subsequently (i) subjecting the resulting compound of formula (I) to a separation process to isolate (3R,3aS,6aR) hexahydrofuro-[2,3-b]furan-3-ol of formula (Ia):

(Ia)

and/or
(ii) oxidising the resulting compound of formula (I) to form a compound of formula (I'):

(I')

and subsequently reducing the compound of formula (I') to a compound of formula endo (I).

The compounds of formula (I) and (Ia) are particularly useful in the preparation of medicaments. According to a preferred embodiment, the present compounds of formula (I) and (Ia) are used as precursors in the preparation of anti-viral drugs, in particular anti-HIV drugs, more in particular HIV protease inhibitors.

The compounds of formula (I) and (Ia) and all intermediates leading to the formation of said compounds are of particular interest in preparing HIV protease inhibitors as disclosed in Ghosh et al Bioorganic & Medicinal Chemistry Letters 8 (1998) 687-690 and WO 95/24385, WO 99/65870, WO 99/67254, WO 99/67417, WO 00/47551, WO 00/76961, WO 01/25240, U.S. Pat. No. 6,127,372 and EP 0 715 618, all incorporated herein by reference, and in particular, the following HIV protease inhibitors:
[(1S,2R)-3-[[(4-aminophenyl)sulfonyl](2-methylpropyl) amino]-2-hydroxy-1-(phenylmethyl)propyl]-carbamic acid (3R,3aS,6aR)-hexahydrofuro[2,3-b]furan-3-yl ester, namely darunavir referred to above (HIV protease inhibitor 1);
[(1S,2R)-2-hydroxy-3-[[(4-methoxyphenyl)sulfonyl] (2-methylpropyl)amino]-1-(phenylmethyl)propyl]-carbamic acid (3R,3aS,6aR)-hexahydrofuro[2,3-b]furan-3-yl ester (HIV protease inhibitor 2); and
[(1S,2R)-3-[(1,3-benzodioxol-5-ylsulfonyl)(2-methylpropyl)amino]-2-hydroxy-1-(phenylmethyl)propyl]-carbamic acid (3R,3aS,6aR)-hexahydrofuro[2,3-b]furan-3-yl ester (HIV protease inhibitor 3), or any pharmaceutically acceptable addition salt thereof.

Thus, the present invention also relates to HIV protease inhibitors 1, 2 and 3 or any pharmaceutically acceptable salt or prodrug thereof, obtained by using a compound of formula (I) prepared according to the present invention in the chemical synthesis of said HIV protease inhibitors. Such chemical synthesis is disclosed in the literature, for instance in the above patent and literature references.

The compound of formulae (Ia) above can be used, after formation of an activated derivative, to synthesise protease inhibitor 1, namely darunavir of formula (A) above, as described for example in WO2005/063770, the contents of which are incorporated herein by reference, by the following method, which comprises:

(i) introducing an isobutylamino group in a compound of formula (1)

(1)

wherein
PG represents an amino-protecting group;
$R_1$ is hydrogen or $C_{1-6}$alkyl;

(ii) introducing a p-nitrophenylsulfonyl group in the resultant compound of step (i);
(iii) reducing the nitro moiety of the resultant compound of step (ii);
(iv) deprotecting the resultant compound of step (iii); and
(v) coupling the resultant compound of step (iv) with a (3R, 3aS,6aR)-hexahydrofuro[2,3-b]furan-3-yl derivative, to form the compound of formula (A) above.

In one embodiment, the present invention relates to a process for preparing the compound of formula (A), characterized in that said process comprises the steps of: introducing an isobutylamino group in a compound of formula (1');

(1')

to obtain a compound of formula (2');

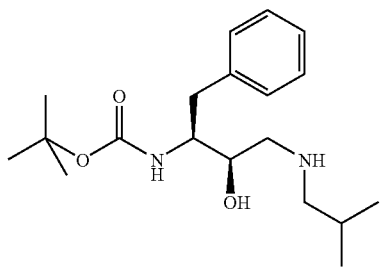
(2')

introducing a p-nitrophenylsulfonyl group into a compound of formula (2') to obtain a compound of formula (3');

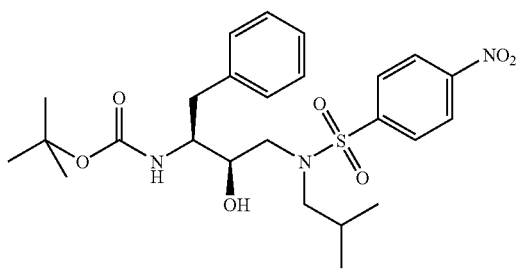
(3')

reducing the nitro moiety of the compound of formula (3') to obtain a compound of

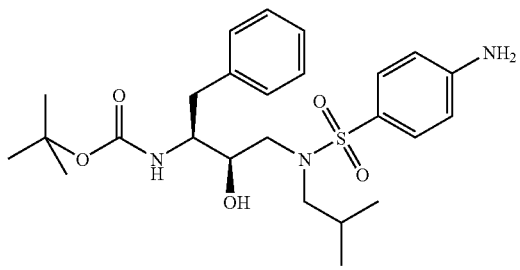
(4')

deprotecting the compound of formula (4') to obtain a compound of formula (5);

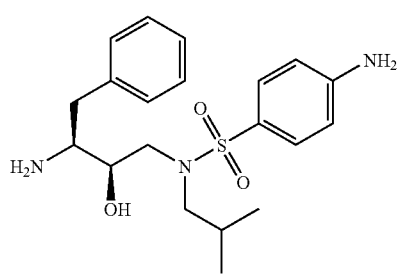
(5)

coupling the compound of formula (5) with a (3R,3aS,6aR)-hexahydrofuro[2,3-b]furan-3-yl derivative to obtain the compound of formula (A).

Compound of Formula (1)

The compound of formula (1) is

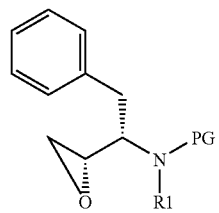
(1)

wherein
PG represents an amino-protecting group;
$R_1$ is hydrogen or $C_{1-6}$alkyl.

Preferably the compound of formula (1) is a compound of formula (1') as shown below wherein PG is a tert-butyloxycarbonyl or "Boc", and $R_1$ is hydrogen. Compounds of formula (1) and (1') are commercially available and may be prepared in several ways available in the literature, for example as described in WO95/06030 (Searle & Co.), as described by Kaneka Corporation in EP0754669 EP1029856 and EP1067125, and as disclosed by Ajinomoto KK in EP1081133 and EP1215209.

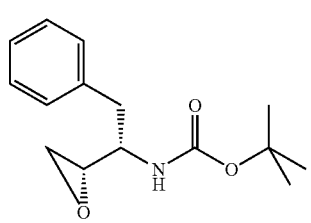
(1')

Compound of Formula (2)

The compound of formula (1) is subjected to an amination on the epoxide to obtain the compound of formula (2).

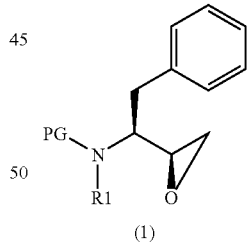
(1)

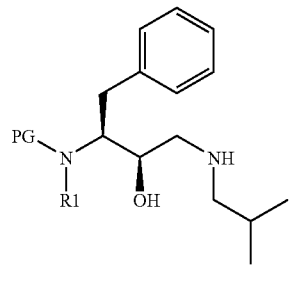
(2)

The term "amination" as used herein refers to a process in which a primary amine, isobutylamine, is introduced into the organic molecule of formula (1). Amination of compound of formula (1) may be accomplished in several ways available in the literature, for example as described in WO95/06030, which is incorporated herein by reference.

In a preferred embodiment, the compound of formula (1') is reacted with isobutylamine to yield the compound of formula (2').

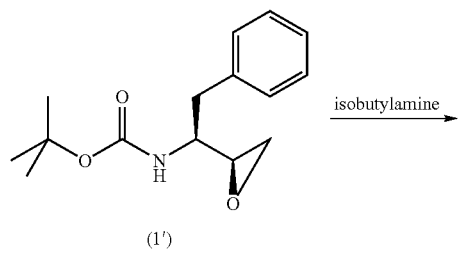

(1')

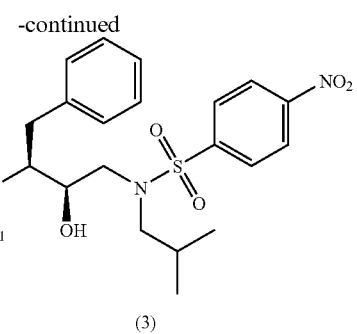

(3)

Thus, in a preferred embodiment the compound of formula (3') will be prepared by sulfonylating the compound of formula (2').

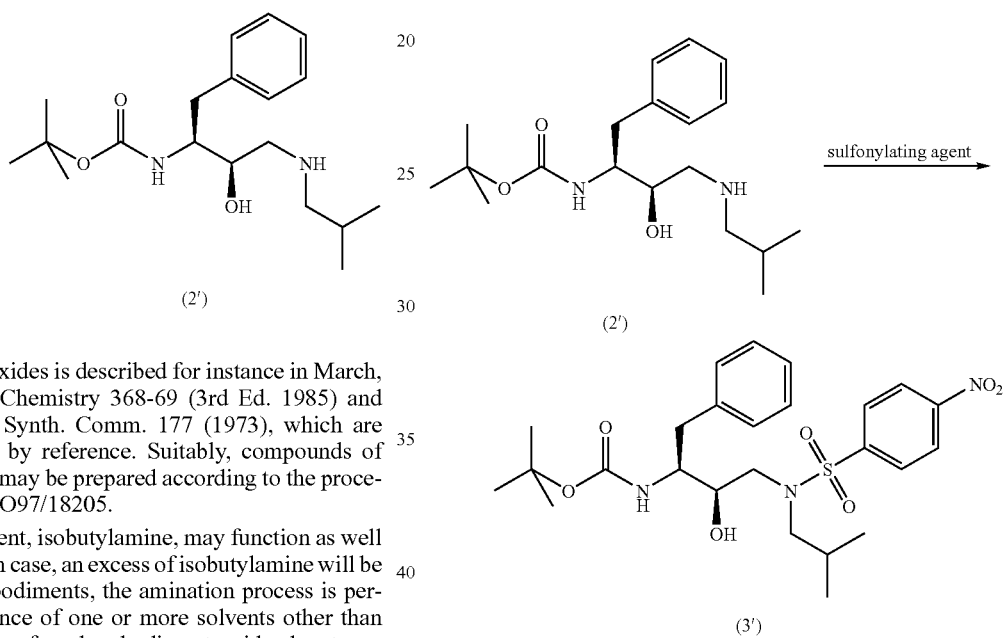

Amination of epoxides is described for instance in March, Advanced Organic Chemistry 368-69 (3rd Ed. 1985) and McManus et al., 3 Synth. Comm. 177 (1973), which are incorporated herein by reference. Suitably, compounds of formula (2) and (2') may be prepared according to the procedure described in WO97/18205.

The amination agent, isobutylamine, may function as well as a solvent, in which case, an excess of isobutylamine will be added. In other embodiments, the amination process is performed in the presence of one or more solvents other than isobutylamine. In a preferred embodiment, said solvents are used in the work-up of compounds of formula (2) and (2').

In an embodiment of the invention, the amination reaction is carried out in the presence of about 15 equivalents of isobutylamine, using toluene as solvent, and heating to reflux at about 79° C.

Compounds of Formula (3)

The compound of formula (3) is prepared by introducing the sulfonyl moiety, p-nitrobenzene-SO$_2$, into the intermediate of formula (2).

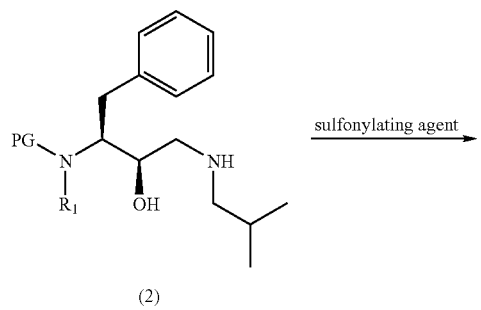

(2)

As such, the compounds of formula (2) and (2') will react with a sulfonylating agent to transform into compounds of formula (3) and (3').

The term "sulfonylating agent" includes p-nitrobenzenesulfonyl derivatives, such as p-nitrobenzenesulfonyl halo-derivatives.

The treatment of compounds of formula (2) and (2') with the sulfonylating agent can be carried out in the presence of a solvent under heating, approximately between 25° C. to 250° C., preferably between 70° C. and 100° C. and agitation. After the sulfonylation, any remaining sulfonylating agent or salts are preferably, although not necessarily, removed from the reaction mixture. This removal can be accomplished by repeated washing with water, change of pH, separation of organic and aqueous phases, ultrafiltration, reverse osmosis, centrifugation, and/or filtration or the like.

Compounds of Formula (4)

The compounds of formula (4) and (4') are obtained by reducing the nitro moiety of the intermediates of formula (3) and (3') respectively with a reducing agent, optionally under a hydrogen atmosphere.

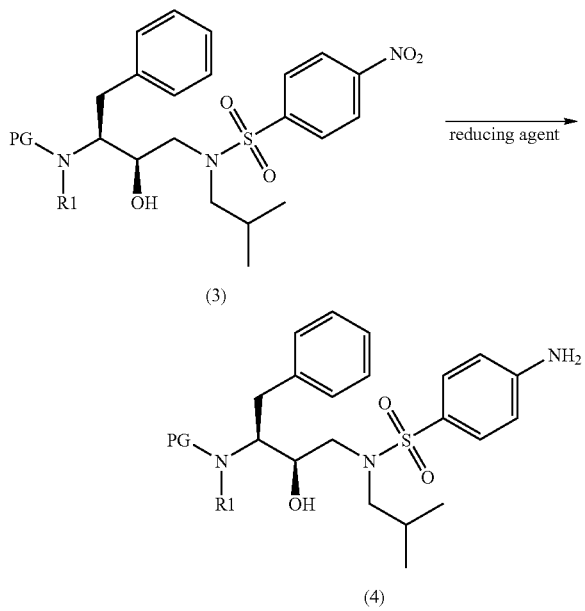

(3)

(4)

Reducing agents suitable for reduction of the nitro moiety are metallic reducing reagents such as borane complexes, diborane, sodium borohydride, lithium borohydride, sodium borohydride-LiCl, aluminum lithium hydride, or diisobutyl-aluminium hydride; metals such as iron, zinc, tin and the like; and transition metals such as palladium-carbon, platinum oxide, Raney-nickel, rhodium, ruthenium and the like. When catalytic reduction is applied, ammonium formate, sodium dihydrogenphosphate, hydrazine may be used as the hydrogen source.

Compounds of Formula (5)

The compound of formula (5) is obtained by deprotecting the intermediates of formula (4) and (4') under conventional acidic conditions. Alternatively basic conditions may be applied.

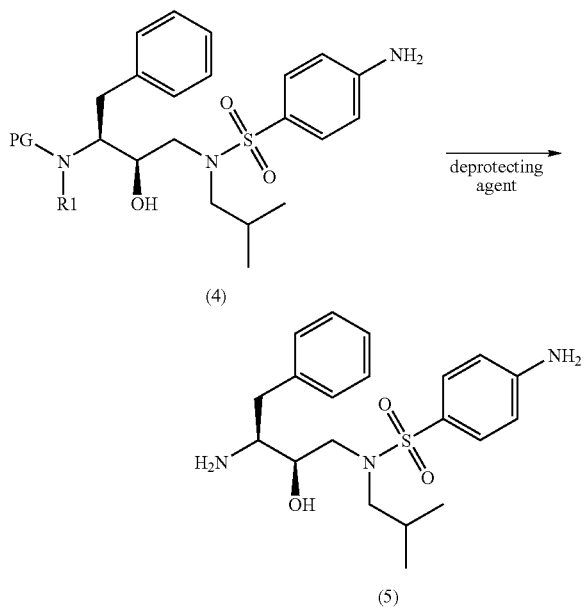

(4)

(5)

Removal of the amino-protecting-group can be achieved using conditions which will not affect the remaining portion of the molecule. These methods are well known in the art and include acid hydrolysis, hydrogenolysis and the like, thus using commonly known acids in suitable solvents.

Examples of reagents and methods for deprotecting amines from amino protecting groups can additionally be found in *Protective Groups in Organic Synthesis* by Theodora W. Greene, New York, John Wiley and Sons, Inc., 1981, incorporated herein by reference.

As those skilled in the art will recognize, the choice of amino protecting group employed in a previous step of the process will dictate the reagents and procedures used in removing said amino protecting group.

Preparation of Darunavir (3R,3aS,6aR)-hexahydrofuro[2,3-b]furan-3-ol of formula (Ia) prepared as described above is suitably activated with a coupling agent to generate a (3R,3aS,6aR)-hexahydrofuro[2,3-b]furan-3-yl derivative which is then carbamoylated with a compound of formula (5) to obtain the desired the protease inhibitor 1, namely darunavir.

Examples of coupling agents used in carbamoylation reactions are carbonates such as bis-(4-nitrophenyl)carbonate, disuccinimidyl carbonate (DSC), carbonyl diimidazole (CDI). Other coupling agents include chloroformates, such as p-nitrophenylchloroformate, phosgenes such as phosgene and triphosgene.

In particular, when the (3R,3aS,6aR)-hexahydrofuro[2,3-b]furan-3-ol is reacted with disuccinimidyl carbonate, 1-([[(3R,3aS,6aR)hexahydrofuro[2,3-b]furan-3-yloxy]-carbonyl]oxy)-2,5-pyrrolidinedione is obtained. Said compound is a preferred (3R,3aS,6aR)-hexahydrofuro[2,3-b]furan-3-yl derivative.

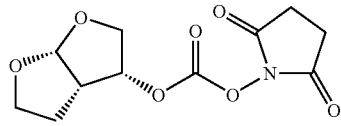

Reaction of the (3R,3aS,6aR)-hexahydrofuro[2,3-b]furan-3-yl derivative with the compound of formula (5) will be performed in the presence of suitable solvents, such as tetrahydrofuran, dimethylformamide, acetonitrile, dioxane, dichloromethane or chloroform, and optionally with bases, such as triethylamine although further combinations from the solvents and bases hereinabove disclosed are also embodied.

Among the solvents, preferred solvents are aprotic solvents such as tetrahydrofuran, acetonitrile, dimethylformamide, ethyl acetate, and the like.

The above carbamoylation reaction is suitably carried out at a temperature between −70° C. and 40° C., preferably between −10° C. and 20° C.

Accordingly to a particularly preferred feature of the present invention we provide darunavir, namely [(1S,2R)-3-[[(4-aminophenyl)sulfonyl](2-methylpropyl)amino]-2-hydroxy-1-(phenylmethyl)propyl]-carbamic acid (3R,3aS,6aR)-hexahydrofuro-[2,3-b]furan-3-yl ester of formula (A), whenever synthesised using an intermediate of formula (I) and especially an intermediate of formula (Ia) prepared in accordance with the present invention.

EXAMPLES

The following examples are meant to be illustrative of the present invention. These examples are presented to exemplify the invention and are not to be construed as limiting the scope of the invention.

Gas chromatography (GC) was performed under the following conditions: column: 5% phenyl-, 95% methyl-polysiloxane, L=25 m; ID=320 μm; film width=0.52 μm; split injector at 250° C. with 1/50 ratio; injection volume: 1 μL. Program: 5 min. at 50° C. then rate of 15° C./min. to 240° C. for 5 min. total flow: 3.0 mL/min. The quality of the reaction product represents the percentage amount in such product of the desired compound as determined by Flame Ignition Detection (FID) following gas chromatography (GC area %).

In the following Examples "DCM" refers to dichloromethane, "AcOEt" refers to ethyl acetate, THF refers to tetrahydrofuran and "TEMPO" refers to 2,2,6,6-tetramethylpiperidine 1-oxide.

COMPARATIVE EXAMPLE (A) Ethyl hydroxy-(2-ethoxytetrahydrofuran-3-yl)acetate

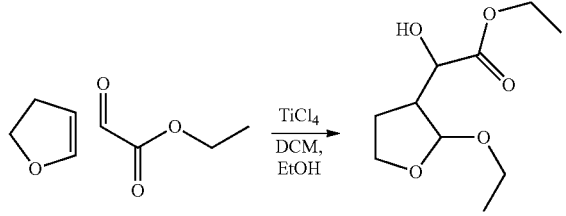

To a mixture of freshly distilled ethyl glyoxalate (40 mmoles; 1.000 equiv; 3.620 mL; 4.084 g) and 2,3-dihydrofuran (44 mmoles; 1.100 equiv; 3.338 mL; 3.084 g) in dry dichloromethane (100 mL; 1.560 moles; 132.5 g) was added dropwise a solution of titanium tetrachloride (44 mmoles; 1.100 equiv; 44.00 mL; 59.84 g) in 1M DCM at −78° C. and the resulting mixture was stirred for 1 h. The reaction mixture turns yellow and heterogeneous. Ethanol (120 mmoles; 3.000 equiv; 6.986 mL; 5.528 g) was added dropwise to the mixture which turned homogeneous. The cooling bath was removed to allow the reaction to warm to room temperature for 1 hour. Sodium bicarbonate (100 mL; 103.4 mmoles; 104.7 g) was added slowly at room temperature.

After 10 min., the reaction mixture was extracted twice with ethyl acetate (600 mL; 6.132 moles; 540.2 g). The organic solvent was evaporated under reduced pressure to afford a green oil containing white solids (9.45 g, GC: 14 area %).

GC: r.t.: 13.4 min.
MS (E.I. 70 eV): 217 (0.5%; M−H); 173 (11%, M-OEt); 155 (59%, 173-H$_2$O); 145 (21%, M-CO$_2$Et); 71 (100%, 173-CHOCO$_2$Et).

From this crude mixture, the titanium determination was performed using an ICP (Inductive Coupled Plasma) method: 96 ppm of titanium.

(B) Attempted Reduction of Product from (A)

In a 50 mL round bottom flask charged with ethanol (9.6 mL) and sodium tetrahydroborate (1.1 equiv; 5.46 mmoles; 210 mg) at 0° C., ethyl hydroxy-(2-ethoxytetrahydrofuran-3-yl)acetate (1.44 g; 4.96 mmoles; 1 equiv.) dissolved in ethanol (5.8 mL) was added dropwise over 1 hour. The reaction mixture was allowed to warm up to room temperature and stirred over a weekend. Then ammonium chloride (1.5 equiv; 7.44 mmoles; 400 mg]) dissolved in water (3.5 mL) was added dropwise to the reaction mixture at 0° C. The reaction mixture was stirred for 4 h at room temperature and the solvent was evaporated under reduced pressure to afford an brown solid. Then ethyl acetate (7.7 mL) was added to the crude mixture and warmed at 40° C. for 30 minutes. After filtration over dicalite the homogenous mixture was evaporated to dryness under reduced pressure to afford the starting material.

Example 1

Ethyl hydroxy-(2-isopropoxytetrahydro-3-furanyl)acetate

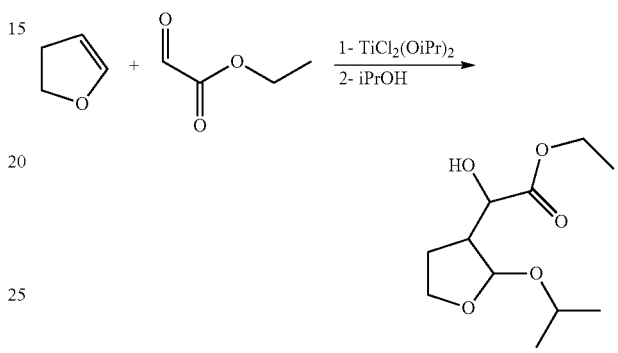

In a round bottom flask, ethyl glyoxylate 50% w/w in toluene (4.74 g, 23.21 mmol, 1.1 eq.) was stirred under reduced pressure at 60° C. until all the toluene was evaporated. Then 80 mL of dry DCM were added at room temperature followed by the addition of TiCl$_2$(OiPr)$_2$ (5 g, 21.1 mmol). After a 0.5 hour stirring period at room temperature, 2,3-dihydrofuran (1.48 g, 21.1 mmol, 1 eq.) dissolved in 15 mL of DCM was added dropwise over 10 min and the mixture was stirred for 5 hours at room temperature. Then isopropanol (16 mL, 211 mmol, 10 eq.) was added dropwise and the mixture was stirred overnight. Finally, a basic aqueous mixture of Rochelle salt (20 g in 200 mL of water, 2 g of Na$_2$CO$_3$) was added dropwise at room temperature and stirred overnight. The two layers were separated, and the organic layer was dried with Na$_2$SO$_4$ and reduced under vacuum. The obtained oil (3.45 g, CG: 85 area %) may be used directly in the next step.

Titanium determination: <5 ppm.
MS (E.I. 70 eV): 173 (16%, M-O$^i$Pr); 159 (22%, M-CO$_2$Et); 155 (100%, 173-H$_2$O); 71 (98%, 173-CHOCO$_2$Et).
MS (C.I., ammonia): (M+H)$^+$: 233.1353 (theory: 233.1389); (M+NH$_4$)$^+$: 250.1593 (theory: 250.1654)

Example 2

Ethyl hydroxy-(2-isopropoxytetrahydro-3-furanyl)acetate

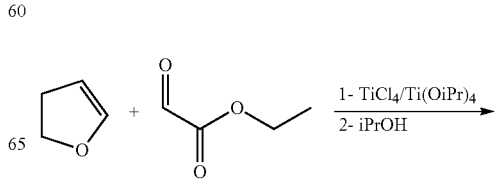

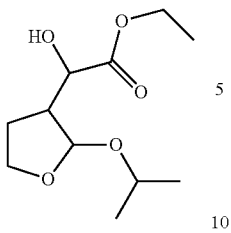

In a 1 L round button flask, titanium tetrachloride (17.83 mmoles; 1.96 mL; 3.38 g) was dissolved in dichloromethane (70 mL; 1.092 moles; 92.75 g) at room temperature. Then titanium tetra(isopropoxide) (17.83 mmoles; 5.28 mL; 5.07 g) dissolved in dichloromethane (70 mL; 1.092 moles; 92.75 g) was added dropwise at room temperature. After a 1 hour stirring period, ethyl glyoxalate (1.1 equiv; 39.24 mmoles; 3.55 mL; 4.0 g) free of toluene, dissolved in dichloromethane (8.75 mL; 136.5 mmoles; 11.59 g) was added dropwise over 30 min at room temperature. After 15 min., 2,3-dihydrofuran (2.5 g; 1.000 equiv; 35.67 mmoles; 2.70 mL) dissolved dichloromethane (17.5 mL; 273.0 mmoles; 23.19 g) was added over 30 min. at room temperature. After a 3 hours stirring period, isopropyl alcohol (10 equiv; 356.7 mmoles; 27.26 mL; 21.44 g) was added dropwise. After 3 hours, the mixture of potassium carbonate (1.75 g; 12.66 mmoles) and Rochelle salt (17.5 g; 83.25 mmoles) dissolved in water (175 mL; 9.72 moles; 175 g) was added to the reaction mixture. After stirring over weekend, the two layers were separated and the organic layer was washed with (2×100 mL) of water (200 mL; 11.10 moles; 200.0 g). The organic solvent was evaporated over reduced pressure to afford the desired product (7.48 g; GC: 92 area %).

Titanium Determination:

before Rochelle salt treatment: 14.5%; after Rochelle salt treatment: <5 ppm $^1$H NMR (CDCl$_3$, 400 MHz): 5.23 (d, 0.42H, J=4 Hz); 5.20 (d, 0.48H, J=2 Hz); 5.16-5.08 (m, 0.14H); 4.45 (d, 0.42H, J=4 Hz); 4.30-4.15 (m, 3H); 4.11-3.96 (m, 0.8H); 3.96-3.81 (m, 2.85H); 3.54 (bs, 0.4H); 2.97 (bs, 0.60H); 2.60-2.42 (m, 1.1H); 2.28-2.15 (m, 0.49H); 1.97-1.79 (m, 1.79H); 1.30 (t, 3.8H, J=8 Hz); 1.24-1.21 (m, 0.46H); 1.21-1.16 (m, 3.12H); 1.16-1.12 (m, 3H).

$^{13}$C NMR (CDCl$_3$, 400 MHz): 174.1; 172.9; 103.9; 102.2; 70.2; 69.6; 69.4; 66.6; 61.9; 61.2; 49.9; 47.0; 25.1; 23.9; 23.7; 21.9; 21.7; 14.2.

Example 3

Ethyl hydroxy-(2-isopropoxytetrahydro-3-furanyl)acetate

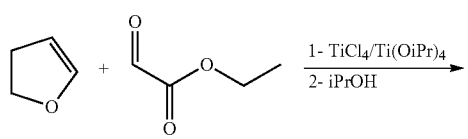

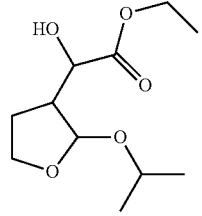

In a 1 L round button flask, titanium tetrachloride (17.83 mmoles; 1.96 mL; 3.38 g) was dissolved in dichloromethane (70 mL; 1.092 moles; 92.75 g) at room temperature. Then titanium tetra(isopropoxide) (17.83 mmoles; 5.28 mL; 5.07 g) dissolved in dichloromethane (70 mL; 1.092 moles; 92.75 g) was added dropwise at room temperature. After a 1 hour stirring period, ethyl glyoxalate (1.1 equiv; 39.24 mmoles; 3.55 mL; 4.0 g) free of toluene, dissolved in dichloromethane (8.75 mL; 136.5 mmoles; 11.59 g) was added dropwise over 30 min at room temperature. After 15 min., 2,3-dihydrofuran (2.5 g; 1.000 equiv; 35.67 mmoles; 2.70 mL) dissolved in dichloromethane (17.5 mL; 273.0 mmoles; 23.19 g) was added over 30 min. at room temperature. After a 3 hours stirring period, isopropyl alcohol (10 equiv; 356.7 mmoles; 27.26 mL; 21.44 g) was added dropwise. After 3 hours, the mixture of potassium carbonate (1.75 g; 12.66 mmoles) and diethanolamine (9.5 g; 90.6 mmoles) dissolved in water (175 mL; 9.72 moles; 175 g) was added to the reaction mixture. After stirring over a weekend, the two layers were separated and the organic layer was washed with (2×100 mL) of water (200 mL; 11.10 moles; 200.0 g). The organic solvent was evaporated over reduced pressure to afford the desired product (7.0 g; GC: 96 area %).

Titanium Determination:

after diethanolamine treatment: <5 ppm

Example 4

Ethyl hydroxy-(2-isopropoxytetrahydro-3-furanyl)acetate

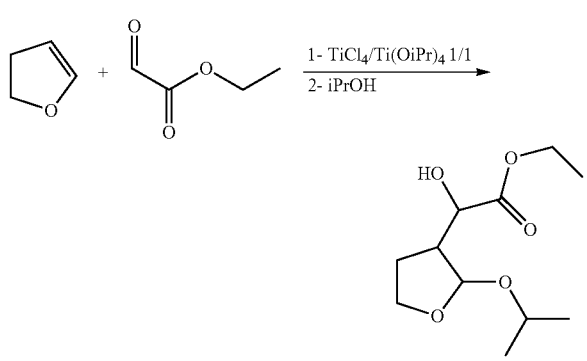

In a round bottom flask charged with 400 mL of DCM and Ti(OiPr)$_4$ (56.8 g, 0.2 mol), TiCl$_4$ (22 mL, 0.2 mol) dissolved in 400 mL of DCM was added dropwise at room temperature over 30 min. After a 17 hour stirring period, ethyl glyoxylate free of toluene (45.2 g, 0.22 mol, 1.1 eq.) dissolved in 50 mL of DCM was added dropwise at room temperature. After 15 min., 2,3-dihydrofuran (14 g, 0.2 mol, 1 eq.) dissolved in 100 mL of DCM was added dropwise over 30 min and the mixture was stirred for 3 hours at room temperature. Then iso-propanol (153 mL, 2 mol, 10 eq.) was added dropwise and the mixture was stirred for 4 hours at room temperature. Finally, a basic aqueous mixture of Rochelle salt (100 g in 1000 mL of water, 10 g $K_2CO_3$) was added dropwise and the resulting mixture stirred overnight at room temperature. The two layers were separated and the organic layer was dried with $Na_2SO_4$, filtered and evaporated under vacuum. The obtained oil (47.2 g, GC: 87 area %) may be used directly in the next step.

GC: r.t.: 13.7 min.

MS (E.I. 70 eV): 173 (16%, M-O$^i$Pr); 159 (22%, M-CO$_2$Et); 155 (100%, 173-H$_2$O); 71 (98%, 173-CHOCO$_2$Et).

MS (C.I., ammonia): (M+H)$^+$: 233.1353 (theory: 233.1389); (M+NH$_4$)$^+$: 250.1593 (theory: 250.1654).

Example 5

Ethyl hydroxy-(2-isopropoxytetrahydro-3-furanyl)acetate

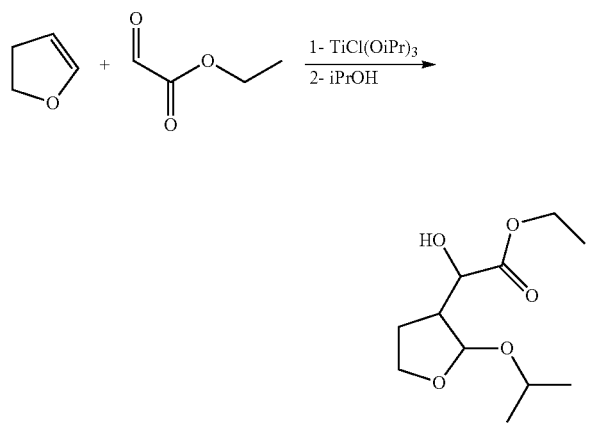

In a round bottom flask charged with TiCl(OiPr)$_3$ (0.1 mol, 1M in hexanes.) and 300 mL of DCM, ethyl glyoxylate free of toluene (22.6 g, 0.11 mol, 1.1 eq.) dissolved in 25 mL of DCM was added dropwise at room temperature. After a 0.5 hour stirring period at room temperature, 2,3-dihydrofuran (7 g, 0.1 mol, 1 eq.) dissolved in 50 mL of DCM was added dropwise over 30 min and the mixture was stirred for 5 hours at room temperature. Then iso-propanol (76 mL, 1 mol, 10 eq.) was added dropwise at room temperature and the mixture was stirred overnight. Finally, a basic aqueous mixture of Rochelle salt (50 g in 500 mL of water, 5 g $K_2CO_3$) was added dropwise at room temperature and stirred overnight. The two layers were separated, the organic layer was dried with $Na_2SO_4$, filtered and evaporated under vacuum. The obtained oil (18.2 g, GC: 85 area %) may be used directly in the next step.

MS (E.I. 70 eV): 173 (16%, M-O$^i$Pr); 159 (22%, M-CO$_2$Et); 155 (100%, 173-H$_2$O); 71 (98%, 173-CHOCO$_2$Et).

MS (C.I., ammonia): (M+H)$^+$: 233.1353 (theory: 233.1389); (M+NH$_4$)$^+$: 250.1593 (theory: 250.1654).

Example 6

Ethyl hydroxy-(2-isopropoxytetrahydro-3-furanyl)acetate

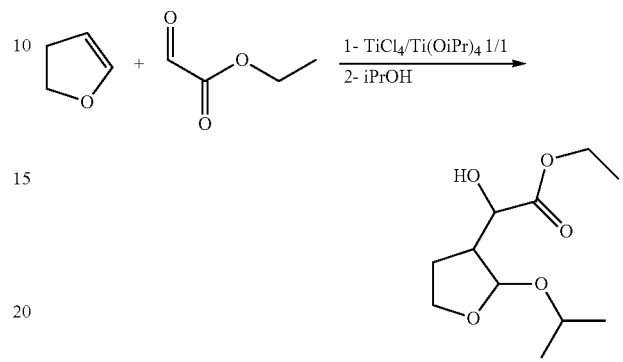

In a round bottom flask charged with 400 mL of DCM and Ti(OiPr)$_4$ (28.4 g, 0.1 mol,), TiCl$_4$ (11 mL, 0.1 mol) dissolved in 400 mL of DCM was added dropwise at room temperature for 30 min. After a 17 hour stirring period, ethyl glyoxylate free of toluene (90 g, 0.44 mol, 1.1 eq.) dissolved in 150 mL of DCM was added dropwise at room temperature over 30 min. After 15 min., 2,3-dihydrofuran (28 g, 0.4 mol, 1 eq.) dissolved in 150 mL of DCM was added dropwise over 30 min at room temperature and the mixture was stirred for 5 hours. Then iso-propanol (306 mL, 4 mol, 10 eq.) was added dropwise at room temperature and the mixture was stirred for 3 hours. Finally, a basic aqueous mixture of Rochelle salt (100 g in 1000 mL of water, 10 g $K_2CO_3$) was added dropwise at room temperature and stirred overnight. The two layers were separated, the organic layer was dried with $Na_2SO_4$, filtered and evaporated under vacuum. The obtained oil (81.5 g, GC: 70 area %) may be used directly in the next step.

GC: r.t.: 13.7 min.

MS (E.I. 70 eV): 173 (16%, M-O$^i$Pr); 159 (22%, M-CO$_2$Et); 155 (100%, 173-H$_2$O); 71 (98%, 173-CHOCO$_2$Et).

MS (C.I., ammonia): (M+H)$^+$: 233.1353 (theory: 233.1389); (M+NH$_4$)$^+$: 250.1593 (theory: 250.1654).

Example 7 a) 1-(2-iso-Propoxytetrahydro-3-furanyl)-1,2-ethanediol

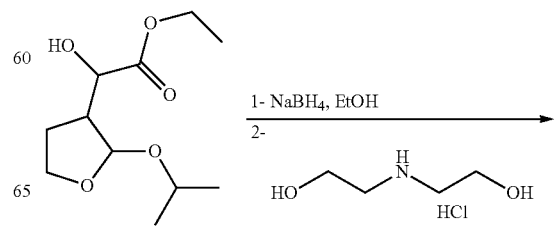

-continued

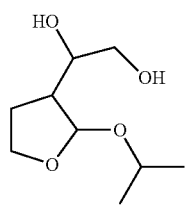

In a 2 L round bottom flask charged with 600 mL of ethanol and NaBH₄ (12.55 g, 0.33 mol, 1.1 eq.) at 0° C., ethyl hydroxy-(2-isopropoxytetrahydro-3-furanyl)acetate (70 g, 0.3 mol, 1 eq.) dissolved in 400 mL of ethanol was added dropwise over 1 hour at 0° C. The mixture was allowed to warm up at room temperature and stirred for 19 hours. After cooling at 0° C., diethanolamine hydrochloride (46.7 g, 0.33 mol, 1.1 eq.) dissolved in 100 mL of water was added over 10 min. and stirred for 8 hours. The solvent was evaporated under reduced pressure to afford a clear yellow solid. After dilution with 300 mL of ethylacetate, the heterogeneous mixture was filtered over dicalite. The mixture was used directly in the next step.

b) 1-(2-iso-Propoxytetrahydro-3-furanyl)-1,2-ethanediol

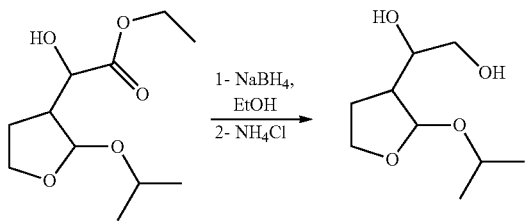

In a round bottom flask charged with ethanol (50 mL) and NaBH₄ (1.066 g, 28.19 mmoles, 1.1 equiv) at 0° C., ethyl hydroxy-(2-isopropoxytetrahydro-3-furanyl)-acetate (7.44 g, 25.62 mmoles, 1.000 equiv) dissolved in ethanol (30 mL) was added dropwise over 1 hour at 0° C. The mixture was allowed to warm up to room temperature and stirred over a weekend. Then ammonium chloride (2.056 g, 38.44 mmoles, 1.5 equiv) dissolved in water (18 mL) was added dropwise to the reaction mixture at 0° C.

The reaction mixture was stirred for 4 h at room temperature and the solvent was evaporated under reduced pressure to afford an brown solid. Then ethyl acetate (40 mL) was added to the crude mixture and warmed at 40° C. for 30 minutes. After filtration over dicalite the homogenous mixture was evaporated to dryness under reduced pressure to afford the desired product (4.39 g,; 19.61 mmoles, 0.7655 equiv, 76.55% yield).

Mixture of Diastereoisomers:

¹H NMR (CDCl₃, 400 MHz): 5.85 (d, J=8 Hz, 0.11H); 5.11-4.86 (m, 2H); 4.3-3.6 (m, 7.7H); 3.8-3.5 (m, 3H); 3.45 (m, 3.7H); 2.49-2.0 (m, 3.4H); 1.95-1.5 (m, 2.34); 1.28 (m, 1.1H); 1.20-1.12 (m, 6H).

¹³C: NMR (CDCl₃; 100 MHz): (main peaks) 109.0; 108.2; 105.8; 105.5; 72.6; 69.6; 69.4; 67.8; 66.9; 63.3; 63.1; 63.0; 49.0; 48.7; 32.4; 28.9; 27.6; 26.4; 23.6; 21.8; 21.8; 15.2; 14.2.

GC: peaks of different isomers @ 5.7 min. 17%; 6.07 min. 8.29%; 6.32 min. 15.7%; 6.7 min. 20.29%; 6.9 min. 11.0%; 10.6 min. 7.6%; 10.8 min. 5%.

Example 8

Hexahydrofuro[2,3-b]furan-3-ol

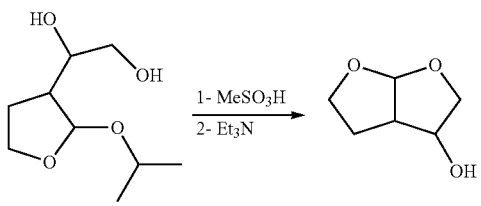

In a 50 mL round bottom flask, 1-(2-iso-propoxytetrahydro-3-furanyl)-1,2-ethanediol (2.21 g; 8.89 mmoles, 1 eq.) was dissolved in tetrahydrofuran (9 mL). After cooling at 0° C., methanesulfonic Acid (65 mg; 676.33 mmoles) was added to the mixture. The reaction mixture was thereafter heated at 45° C. for 30 min. After cooling at room temperature, triethylamine (0.3 g; 2.96 mmoles) was added to the mixture. The solvent was evaporated and ethyl acetate (9 mL; 91.98 mmoles) was added to the mixture at room temperature. Then the mixture was filtered over dicalite and the solvent was evaporated under reduced pressure to afford endo/exo bis-THF (1.562 g; GC: 71 area %) in a diastereomeric ratio of 15/85 endo/exo diastereoisomers.

The two diastereoisomers were separated by chromatography on silica gel:eluant:AcOEt./hexane 9/1.

GC: exo hexahydrofuro[2,3-b]furan-3-ol: r.t.: 11.36 min.; endo hexahydrofuro[2,3-b]-furan-3-ol: r.t. 11.57 min.

¹H NMR:

exo hexahydrofuro[2,3-b]furan-3-ol: 1.67 (m, 1H); 2.13 (m, 1H); 2.31 (bs, 1H); 2.79 (m, 1H); 3.8-3.9 (m, 3H); 2.95 (dd, 1H, J=3.2 Hz, J=10.3 Hz); 4.2 (d, 1H, J=3.1 Hz); 5.9 (dd, 1H, J=4.9 Hz).

endo hexahydrofuro[2,3-b]furan-3-ol: 1.85 (m, 1H); 1.94 (bs, 1H); 2.27 (m, 1H); 2.84 (m, 1H); 3.6 (dd, 1H, J=7.1 Hz, J=9.2 Hz); 3.89 (m, 1H); 3.97 (m, 1H); 4.43 (dd, 1H, J=6.8 Hz, J=14.5 Hz); 5.68 (d, 1H, J=5.2 Hz).

Example 9 a) Tetrahydrofuro[2,3-b]furan-3(2H)-one

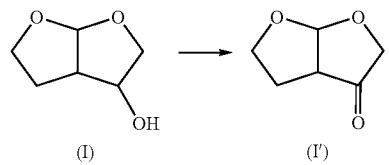

(I)      (I')

In a 250 mL round bottom flask, NaOCl (6.15 g, 14% w/w) was diluted in 100 mL of water. The pH of the solution was adjusted to 9.5 using a 1M NaHCO₃ aqueous solution. In a separate 250 mL round bottom flask, hexahydrofuro[2,3-b] furan-3-ol (1 g, 7.7 mmol, 1 eq.) was dissolved in 15 mL of AcOEt at 0° C. Then KBr (91 mg, 0.77 mmol, 0.1 eq.) dissolved in 1 mL of water was added followed by the addition of TEMPO (12 mg, 0.08 mmol, 0.01 eq.). Finally, the NaOCl mixture was added dropwise. After 15 minutes of stirring at 0° C., the mixture was extracted 3 times with 100 mL of AcOEt. The collected organic layers were dried over $Na_2SO_4$ and the solvent was evaporated under reduced pressure to afford 950 mg of a white solid, yield: 96%. The resulting tetrahydrofuro[2,3-b]furan-3(2H)-one was used in the next step without further purification.

The product was identified by accurate mass: m/z: 128.0473 (theoretical mass: 128.0473).

b) Stereoselective Preparation of (3R,3aS,6aR) hexahydrofuro[2,3-b]furan-3-ol

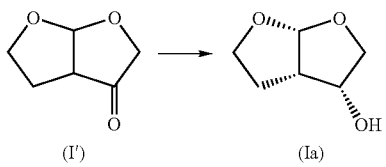

Generally in accordance with the procedure described by Ghosh et al in J. Org. Chem. 2004, 69, 7822-7829, tetrahydrofuro[2,3-b]furan-3(2H)-one (950 mg, 7.42 mmol, 1 eq.) was dissolved at 0° C. in 50 mL of ethanol. $NaBH_4$ (302.4 mg, 8 mmol, 1.07 eq.) was added in one portion to the mixture. After a 1 hour stirring period, diethanolamine hydrochloride salt (3.2 g, 8 mmol, 1.07 eq.) was added and the mixture was stirred overnight at room temperature. The heterogeneous mixture was filtered over dicalite and washed with 20 mL of warm AcOEt. After evaporation of the organic solvents under reduced pressure to afford 1500 mg of hexahydrofuro[2,3-b]furan-3-ol with a quality (area %) of 40%; max yield: 60%. diastereoisomeric excess: exo(3S,3aS,6aR)/endo (3R,3aS,6aR): 18.5/81.5.

The invention claimed is:

1. A process for the preparation of a compound of formula (V) which comprises reacting 2,3-dihydrofuran of formula (II) with a glyoxylate derivative of formula (III) in the presence of a titanium salt of formula $Ti(Hal)_n(OR)_{4-n}$ in which Hal is a halogen radical, n is 0, 1, 2 or 3 and R is alkyl or arylalkyl, and subsequently reacting the resulting reaction product with an alcohol of formula (IV) to form a compound of formula (V):

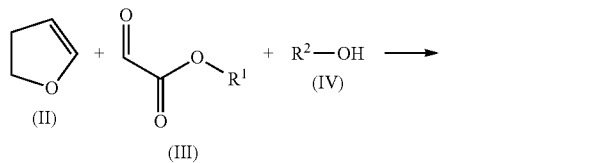

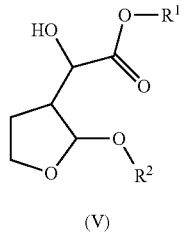

in which $R^1$ is alkyl or arylalkyl and $R^2$ is alkyl or arylalkyl.

2. A process as claimed in claim 1 in which the titanium salt is a compound of formula $Ti(Hal)_n(OR)_{4-n}$ in which n is 1, 2 or 3.

3. A process as claimed in claim 1 in which $R^1$ is $C_{1-4}$ alkyl.

4. A process as claimed in claim 1 in which $R^2$ is $C_{1-4}$ alkyl.

5. A process as claimed in claim 1 in which 2,3-dihydrofuran of formula (II) is reacted with the glyoxylate derivative of formula (III) in the presence of the titanium salt and the subsequent reaction product is reacted with the alcohol of formula (IV) to form a compound of formula (V).

6. A process as claimed in claim 1 in which the resulting reaction mixture containing the compound of formula (V) is treated with Rochelle salt to effect removal of residual titanium compound.

7. A process as claimed in claim 6 in which the treatment with Rochelle salt is effected in an alkaline medium.

8. Compounds of formula (Va):

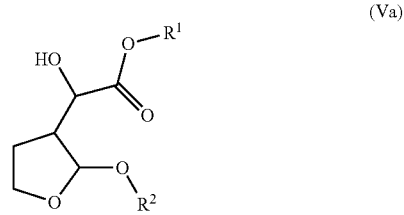

and the stereoisomeric forms and racemic mixtures thereof, in which $R^1$ is alkyl or arylalkyl and $R^2$ is alkyl or arylalkyl, providing that when $R^2$ is methyl $R^1$ is not methyl or ethyl.

9. Ethyl hydroxy-(2-isopropoxytetrahydro-3-furanyl)acetate.

10. A process for the preparation of compounds of formula (VI) which comprises reducing a compound of formula (V) to form a compound of formula (VI):

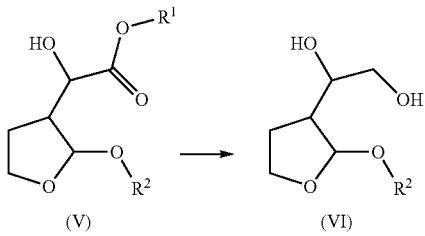

in which $R^1$ and $R^2$ are as defined in claim 1.

11. A process as claimed in claim 10 in which the reduction is effected with a borohydride reducing agent.

12. Compounds of formula (VI):

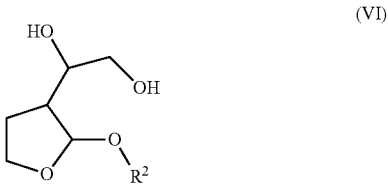

in which $R^2$ is as defined in claim 1.

13. 1-(2-iso-Propoxytetrahydro-3-furanyl)-1,2-ethanediol.

14. A process for the preparation of a compound of formula (I) which comprises cyclising a compound of formula (VI) to form a compound of formula (I):

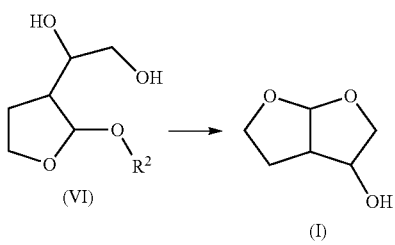

15. A process as claimed in claim 14 in which the cyclisation of the compound of formula (VI) is effected by treatment with a strong protic acid.

16. A process for the preparation of hexahydrofuro[2,3-b]furan-3-ol of formula (I) which comprises the stages of:

a) reacting 2,3-dihydrofuran of formula (II) with a glyoxylate derivative of formula (III) in the presence of a titanium salt of formula Ti(Hal)$_n$(OR)$_{4-n}$ in which n is 0, 1, 2 or 3 and R is alkyl or arylalkyl, and subsequently reacting the resulting reaction product with an alcohol of formula (IV) to form a compound of formula (V):

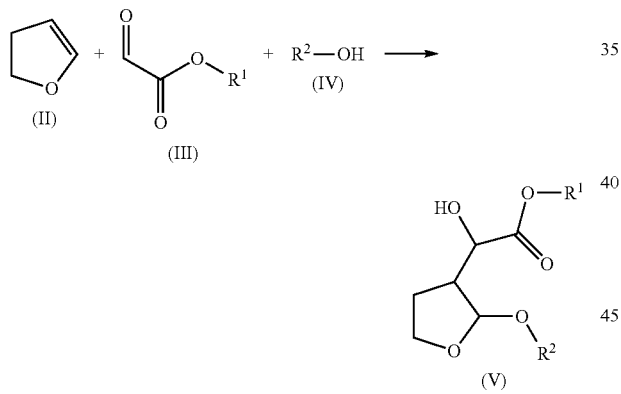

in which R$^1$ is alkyl or arylalkyl and R$^2$ is alkyl or arylalkyl; and b) reducing the resulting compound of formula (V) to form a compound of formula (VI):

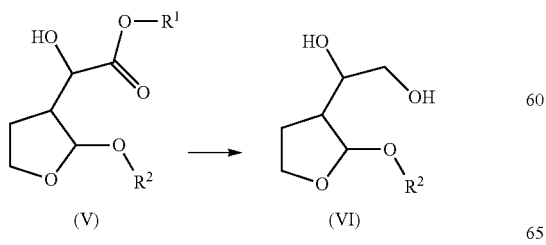

and c) cyclising a compound of formula (VI) to form a compound of formula (I):

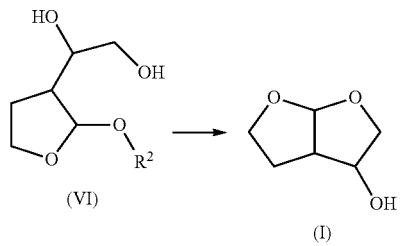

and if desired subsequently (i) subjecting the resulting compound of formula (I) to chiral separation to isolate (3R,3aS,6aR) hexahydrofuro-[2,3-b]furan-3-ol of formula (Ia):

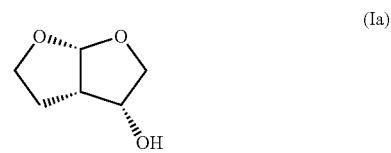

and/or (ii) oxidising the resulting compound of formula (I) to form a compound of formula (I'):

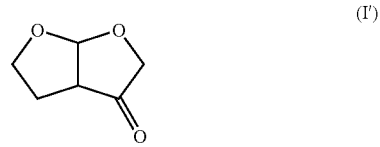

and subsequently reducing the compound of formula (I') to a compound of formula (Ia).

17. A method of preparing [(1S,2R)-3-[[(4-Aminophenyl)sulfonyl](2-methylpropyl)amino]-2-hydroxy-1-(phenylmethyl)propyl]-carbamic acid (3R,3aS,6aR)-hexahydrofuro[2,3-b]furan-3-yl ester comprising:

(a) preparing a hexahydrofuro[2,3-b]furan-3-ol of formula (I):

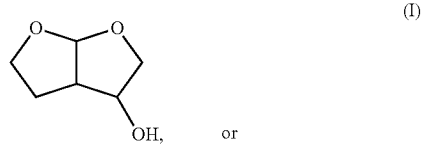

(3R,3aS,6aR) hexahydrofuro-[2,3-b]furan-3-ol of formula (Ia)

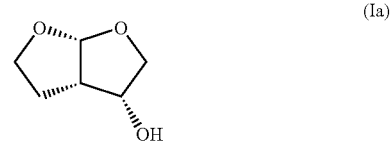

from a compound of formula (V) produced by the process of claim 1:

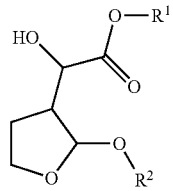

in which R¹ is alkyl or arylalkyl and R² is alkyl or arylalkyl by reducing a compound of formula (V) to form a compound of formula (VI):

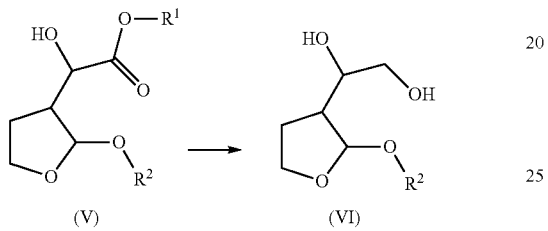

and cyclising the compound of formula (VI) to form a compound the formula (I) and optionally subjecting the resulting compound of formula (I) to chiral separation to isolate the compound of formula (Ia);
(b) reacting the compound of formula (I) or formula (Ia) with a coupling agent to generate a hexahydrofuro[2,3-b]furan-3-yl derivative; and
(c) carbamoylating said derivative with a compound of formula (5):

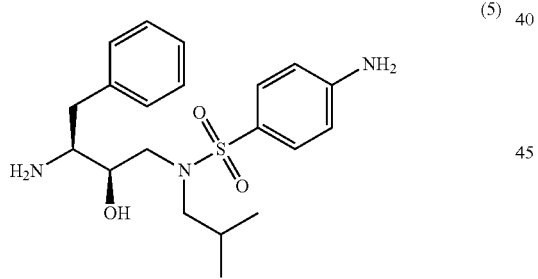

to form the [(1S,2R)-3-[[(4-Aminophenyl)sulfonyl](2-methylpropyl)amino]-2-hydroxy-1-(phenylmethyl)propyl]-carbamic acid (3R,3aS,6aR)-hexahydrofuro[2,3-b]furan-3-yl ester.
18. The method of claim 17 wherein the coupling agent is a carbonate, chloroformate, phosgene or triphosgene.

19. A method of synthesizing [(1S,2R)-3-[[(4-Aminophenyl)sulfonyl](2-methylpropyl)amino]-2-hydroxy-1-(phenylmethyl)propyl]-carbamic acid (3R,3aS,6aR)-hexahydrofuro[2,3-b]furan-3-yl ester comprising:
(a) preparing a hexahydrofuro[2,3-b]furan-3-ol of formula (I):

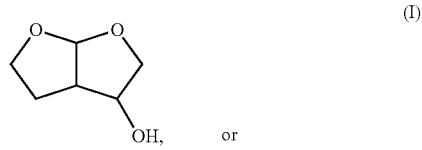

3aS,6aR) hexahydrofuro-[2,3-b]furan-3-ol of formula (Ia):

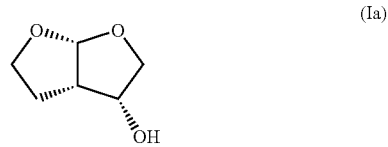

by the process of claim 16;
(b) reacting the compound of formula (I) or formula (Ia) with a coupling agent to generate a hexahydrofuro[2,3-b]furan-3-yl derivative; and
(c) carbamoylating said derivative with a compound of formula (5):

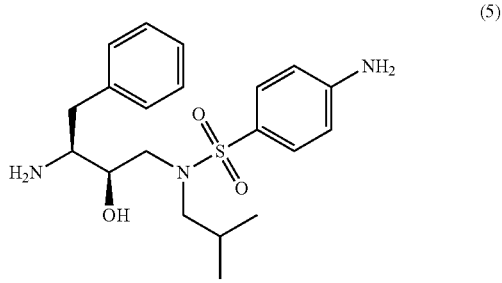

to form the [(1S,2R)-3-[[(4-Aminophenyl)sulfonyl](2-methylpropyl)amino]-2-hydroxy-1-(phenylmethyl)propyl]-carbamic acid (3R,3aS,6aR)-hexahydrofuro[2,3-b]furan-3-yl ester.
20. The method of claim 19 wherein the coupling agent is selected from the group consisting of bis-(4-nitrophenyl)carbonate, disuccinimidyl carbonate (DSC), carbonyl diimidazole (CDI), p-nitrophenylchloro-formate, phosgene and triphosgene.

* * * * *